United States Patent [19]

Pfirmann et al.

[11] Patent Number: 5,478,963
[45] Date of Patent: Dec. 26, 1995

[54] 2,3-DIFLUORO-6-NITROBENZONITRILE AND 2-CHLORO-5,6-DIFLUOROBENZONITRILE-(2,3-DIFLUORO-6-CHLOROBENZONITRILE), PROCESS FOR THEIR PREPARATION AND THEIR USE FOR THE PREPARATION OF 2,3,6-TRIFLUOROBENZOIC ACID

[75] Inventors: Ralf Pfirmann, Griesheim; Theodor Papenfuhs, Frankfurt, both of Germany

[73] Assignee: Hoechst Aktiengesellschaft, Frankfurt, Germany

[21] Appl. No.: 184,039

[22] Filed: Jan. 21, 1994

[30] Foreign Application Priority Data

Jan. 23, 1993 [DE] Germany ............ 43 01 756.8

[51] Int. Cl.⁶ ............................................. C07C 253/14
[52] U.S. Cl. ...................... 558/343; 558/424; 558/425; 562/493
[58] Field of Search ........................... 558/424, 425, 558/343

[56] References Cited

U.S. PATENT DOCUMENTS

| | | | |
|---|---|---|---|
| 4,209,457 | 6/1980 | Fuller | 558/425 |
| 4,225,534 | 9/1980 | Yoshikawa | 558/425 |
| 4,229,365 | 10/1980 | Oeser et al. | 558/424 |
| 4,582,948 | 4/1986 | Tang et al. | 558/425 X |
| 4,590,315 | 5/1986 | Maul et al. | 558/425 X |
| 4,684,734 | 8/1987 | Kaieda et al. | 558/425 X |

FOREIGN PATENT DOCUMENTS

| | | |
|---|---|---|
| 0180057 | 5/1986 | European Pat. Off. . |
| 0334188 | 9/1989 | European Pat. Off. . |
| 433124 | 6/1991 | European Pat. Off. ............ 558/425 |
| 497239 | 8/1992 | European Pat. Off. ............ 558/425 |
| 557949 | 9/1993 | European Pat. Off. ............ 558/425 |
| 91/06530 | 5/1991 | WIPO . |

OTHER PUBLICATIONS

Patent Abstract of Japan, Publication No. JP3090057, Application No. JP890225246, Apr. 16, 1991.

*Primary Examiner*—Joseph Paul Brust
*Attorney, Agent, or Firm*—Connolly & Hutz

[57] ABSTRACT

The present invention describes the novel intermediates 2,3-difluoro-6-nitrobenzonitrile and 2-chloro-5,6-difluorobenzonitrile, a process for their preparation and their advantageous use for the preparation of 2,3,6-trifluorobenzoic acid, which in turn is a valuable intermediate for the preparation of insecticides and antibacterial agents. The intermediates according to the invention are prepared from 2,3,4-trifluoronitrobenzene by fluorine/cyanide exchange and subsequent denitrating chlorination. 2,3,6-Trifluorobenzoic acid can be prepared from the novel intermediates, in a manner known per se in the literature, by simple chlorine/fluorine exchange and subsequent hydrolysis in a process which overall is industrially advantageous and economically favorable.

25 Claims, No Drawings

2,3-DIFLUORO-6-NITROBENZONITRILE AND 2-CHLORO-5,6-DIFLUOROBENZONITRILE-(2,3-DIFLUORO-6-CHLOROBENZONITRILE), PROCESS FOR THEIR PREPARATION AND THEIR USE FOR THE PREPARATION OF 2,3,6-TRIFLUOROBENZOIC ACID

DESCRIPTION 2,3-Difluoro-6-nitrobenzonitrile and 2-chloro-5,6-difluorobenzonitrile (2,3-difluoro-6-chlorobenzonitrile), process for their preparation and their use for the preparation of 2,3,6-trifluorobenzoic acid.

The present invention relates to 2,3-difluoro-6-nitrobenzonitrile and 2-chloro-5,6-difluorobenzonitrile (2,3 -difluoro-6-chlorobenzonitrile), to a process for their preparation and to their use for the preparation of 2,3,6-trifluorobenzoic acid.

2,3,6-Trifluorobenzoic acid is an important intermediate for the synthesis of plant protection agents and drugs. The preparation of pyrethroid pesticides with advantageous properties is described in European patent 498 724 and the conversion to quinolonecarboxylic acid anti-infective agents is known for example from U.S. Pat. No. 4,874,764.

Only uneconomic or industrially impracticable synthetic routes have hitherto been disclosed for the preparation of 2,3,6-trifluorobenzoic acid, for example via the lithiation (halogen/metal exchange) of 2,4,5-trifluorobromobenzene in ethers (J. Org. Chem. 55 (2), 773–775) to give the target compound in 50% yield together with a corresponding proportion of the 2,4,5-isomer, which moreover is very difficult to separate off. The compound was first described by Holland et al. (J. Org. Chem. 29 (1964), 3045), who observed the formation of the compound in 69% yield in mechanistic studies of the reaction of 2,3,5,6-tetrafluoro-4-trifluoromethylphenylhydrazine, itself difficult to obtain, with strong bases. By converting 2,3,4-trichloronitrobenzene via chlorine/fluorine exchange, fluorine/cyanide exchange, subsequent denitrating chlorination and renewed chlorine/fluorine exchange, it is also possible to prepare 2,3,6-trifluorobenzonitrile (Japanese patent 03090057), which can then be hydrolyzed to 2,3,6-trifluorobenzoic acid by processes known in the literature. This process has the particular disadvantage that the probability of forming polychlorinated dibenzodioxins in the first chlorine/fluorine exchange is very high. Furthermore, it is necessary to carry out two chlorine/fluorine exchange (halex) reaction steps to arrive at the product. In addition, the required chlorine/cyanide exchange reaction is unfavorable because of the low activity of the chlorine atom.

Thus there was a need for a novel process or novel intermediates for the preparation of 2,3,6-trifluorobenzoic acid which do not exhibit the disadvantages described.

The invention relates to 2,3-difluorobenzonitriles of formula I:

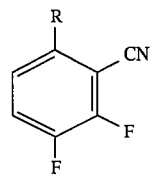

in which R is $NO_2$ or Cl. It further relates to a process for their preparation and to their use for the preparation of 2,3,6-trifluorobenzoic acid.

The process comprises reacting 2,3,4-trifluoronitrobenzene with a cyanide in the presence of a solvent to give 2,3-difluoro-6-nitrobenzonitrile and optionally reacting the 2,3-difluoro-6-nitrobenzonitrile with a chlorinating agent at elevated temperature, optionally in the presence of a fluoride-trapping and/or dehydrating agent, to give 2-chloro-5, 6-difluorobenzonitrile (2,3-difluoro-6-chlorobenzonitrile).

The starting material used in the process according to the invention is 2,3,4-trifluoronitrobenzene, which can be prepared by several economically advantageous and industrially practicable processes (see inter alia Japanese patent 61044831, Japanese patent 63203636) and which is already manufactured industrially in large quantities for the synthesis of quinolonecarboxylic acid antibacterial agents (ofloxacin, lomefloxacin, fleroxacin and many more).

Various cyanides can be successfully used. It is possible to use alkali metal or alkaline earth metal cyanides or cyanides of subgroup elements (transition metals), preferably sodium, potassium or copper cyanide. These cyanides are used in amounts of about 1.0 mol to about 5 mol, preferably about 1.1 mol to about 2 mol, per mol of 2,3,4-trifluoronitrobenzene to be converted.

The reaction with cyanides is carried out in dipolar aprotic solvents such as acetone, tetrahydrofuran (THF), acetonitrile, 1,2-dimethoxyethane (DME), sulfolane (tetramethylene sulfone), tetramethylene sulfoxide (TMSO), N,N-diethylacetamide, N,N-dimethylacetamide (DMAc), N,N-dimethylformamide (DMF), N-methylpyrrolidone (NMP), dimethyl sulfoxide (DMSO), dimethyl sulfone, diphenyl sulfoxide, diphenyl sulfone, tetramethylurea, tetra-n-butylurea, 1,3-dimethylimidazolidin-2-one (DMI) or mixtures thereof. Alternatively, however, it is also possible to use protic solvents such as tertiary alcohols, preferably tert-butanol, or water. A further possibility is to carry out the reaction in excess 2,3,4-trifluoronitrobenzene as the solvent.

The reaction is carried out at temperatures from about 20° to about 120° C., preferably between about 40° and about 80° C.

2,3-Difluoro-6-nitrobenzonitrile can be isolated as a crude product for example by distillation of the bulk of the solvent used and precipitation with water. Purification is conveniently effected by recrystallization with the addition of activated charcoal, but can also be performed by chromatography.

To prepare 2-chloro-5,6-difluorobenzonitrile, 2,3-difluoro-6-nitrobenzonitrile is reacted with a chlorinating agent at elevated temperature, optionally in the presence of a fluoride-trapping and/or dehydrating agent. Denitrating chlorination is known in the literature (European patent 163 230 A3, European patent 355 719 A1, European patent 180 057, European patent 150 587) and has been carried out industrially for a long time. However, it is only described on substrates with substituents which are not easily oxidizable.

In this type of reaction, a strongly corrosive mixture of water, hydrogen halides and nitrous gases is normally produced by the oxidative degradation of part of the starting material. There was therefore a danger that the starting material (2,3-difluoro-6-nitrobenzonitrile), with its relatively complex substituents, would be decomposed more easily than known substrates under the reaction conditions. In view of this, it was surprising that the novel 2,3-difluoro-6-nitrobenzonitrile prepared according to the invention can be converted with high selectivity to replace the nitro group with a chlorine atom, without decomposition reactions or appreciable hydrogen cyanide elimination occurring.

Chlorinating agents which can be used are the conventional agents such as chlorine, phosphorus trichloride or phosphorus pentachloride, especially chlorine.

The replacement of the nitro group with chlorine takes place at temperatures between about 110° and about 200° C. In a particularly simple embodiment, the process is carried out at a bottom temperature of 175° to 190° C., because the reaction rate is already sufficiently high and 2-chloro-5,6-difluorobenzonitrile can optionally be distilled uniformly out of the reaction mixture as a crude product. 0.5 to 20 mol, preferably 0.7 to 3 mol, of chlorinating agent are used per mol of 2,3-difluoro-6-nitrobenzonitrile. The chlorine streams which are preferably used are between about 10 and about 400 ml/g.h, preferably between about 20 and about 200 ml/g.h. This step can preferably be carried out batchwise with distillation of the end product. It can also prove perfectly reasonable here to use less than the stoichiometric amount of chlorine, preferably 20 to 30 percent less than the molar stoichiometric amount, and then to distil off the low-boiling fraction containing the product. In this special case, this procedure with less than the stoichiometric amount of chlorine has disadvantages on account of the relatively high freezing point of the starting material and the danger of exothermic decomposition. It proves convenient to add dehydrating and/or fluoride-trapping agents to the bottom of the chlorination column in order to prevent the hydrogen fluoride corrosion which can occur extensively in such reactions, said agents preferably being calcium salts such as calcium chloride, calcium sulfate and calcium hydroxide, and silicon dioxide. Suitable dehydrating agents are phosphorus pentoxide and phosphorus pentachloride. These additives can optionally account for up to about 10 percent by weight, based on the reactants in the chlorination. It is generally sufficient to use about 2 to about 5% by weight.

A further advantage of the process according to the invention is that the useful product obtained is already sufficiently pure for immediate further processing in conventional manner.

2-Chloro-5,6-difluorobenzonitrile ( 2,3-difluoro-6-chlorobenzonitrile) can advantageously be used for the preparation of 2,3,6-trifluorobenzoic acid.

2-Chloro-5,6-difluorobenzonitrile is first converted to 2,3, 6-trifluorobenzonitrile by a chlorine/fluorine exchange (halex) reaction. This reaction is optionally carried out in a solvent or in a melt of the educt, with alkali metal fluorides at elevated temperatures, optionally in the presence of phase transfer catalysts.

Examples of alkali metal fluorides used are potassium, rubidium or cesium fluoride, or mixtures thereof, in amounts of about 0.8 to about 3 mol of fluoride per mol of 2-chloro-5,6-difluorobenzonitrile, preferably about 0.9 to about 1.5 mol and particularly preferably about 0.95 to about 1.2 mol. Mixtures of potassium and cesium fluorides and pure potassium fluoride are preferred. In the reaction of the novel intermediate according to the invention, the use of spray-dried fluoride salt is tolerated albeit unnecessary for obtaining good results.

The chlorine/fluorine exchange step is conventionally carried out in dipolar aprotic solvents such as sulfolane (tetramethylene sulfone), tetramethylene sulfoxide (TMSO), N,N-diethylacetamide, N,N-dimethylacetamide (DMAc), N,N-dimethylformamide (DMF), N-methylpyrrolidone (NMP), dimethyl sulfoxide (DMSO), dimethyl sulfone, diphenyl sulfoxide, diphenyl sulfone, tetramethylurea, tetra-n-butylurea, 1,3-dimethylimidazolidin-2-one (DMI) or mixtures thereof.

Suitable phase transfer catalysts are quaternary ammonium or phosphonium compounds such as tetra-$C_1$-$C_{18}$-alkylammonium chlorides, bromides or fluorides, tetra-$C_1$-$C_{18}$alkylphosphonium chlorides or bromides, tetraphenylphosphonium chloride or bromide and (phenyl)$_m$($C_1$-$C_{18}$-alkyl)$_n$phosphonium chlorides or bromides, where m=1 to 3, n=3 to 1 and m+n=4. Phosphonium salts are preferred here, especially tetra-$C_1$-$C_{18}$-alkylphosphonium bromides. These substances are used in amounts of about 0.01 to about 50 mol %, based on 2-chloro-5,6-difluorobenzonitrile, preferably between about 0.5 and about 10 mol % and particularly preferably between about 1 and about 5 mol %. Oligo- or polyethylene glycol dimethyl ethers can also be used as phase transfer catalysts. The number of glycol units in these compounds can range from n=4 (tetraethylene glycol dimethyl ether) to about n= 150, but it is preferable to use ethers having a degree of polymerization between about n=4 and about n=25. The optimal required amount of these glycol ethers is between about 0.5% by weight and about 200% by weight, based on the weight of the reaction salt used, preferably between about 5 and about 100% by weight and particularly preferably between about 10 and about 50% by weight. The particular advantage of using these compounds is that it is normally possible to use less solvent, according to the required amount of said compounds, because the glycol ethers are always liquid at the reaction temperature. It is also possible to use mixtures of the above-mentioned phase transfer catalysts in any desired combination. Such a procedure can be advantageous in specific cases.

The operating temperatures are between about 20° and about 250° C., preferably between about 120° and about 200° C. and particularly preferably between about 140° and about 180° C.

The product mixture resulting from this subsequent step is generally obtained by filtration of the reaction salt and, especially when carried out on the industrial scale, subsequent distillation of the readily volatile constituents and fractionation. Direct fractionation from the filtrate is also possible. A further possibility is to add water to the crude mixture and separate off the less dense, upper phase containing the product. Extraction of the water makes it possible to achieve a complete separation of the product from the mother liquor. Purification can then be effected by chromatographic or distillative separation.

The yields are normally about 75 to about 90%, depending on the choice of catalyst, the reaction temperature and the concentration in the solvent.

The hydrolysis of 2,3,6-trifluorobenzonitrile is known in the literature and proceeds completely analogously to the reaction of similar fluorinated benzoic acids (e.g. European patent 433 124, European patent 431 373). The hydrolysis is generally carried out in 70 to 90 percent sulfuric acid to give yields in excess of 90% of theory (H. Henecka in Houben-Weyl-Müller, loc. cit.; also see Example 4).

All the process steps can be carried out under atmospheric pressure, reduced pressure or excess pressure, the procedure with a slight excess pressure being preferred in the denitrating chlorination step. The procedure with a slight excess pressure in a closed vessel, to avoid loss of the readily volatile product, is preferred in the halex reaction step because said product already has a substantial vapor pressure at the reaction temperatures. This effect can be utilized to distil the product off continuously during the reaction, although this demands a more expensive apparatus and control technology (uniform reflux). A subsequent fine fractionation is nevertheless generally required. However, if the reaction conditions, such as catalyst, concentration, temperature and amount of salt, are optimized, this additional expense is found not to be necessary in order to achieve high product yields and space-time yields.

The following Examples illustrate the process without implying a limitation.

Example 1

32.5 g (0.5 mol) of potassium cyanide are placed in 400 g of tert-butanol, and 44.3 g (0.25 mol) of 2,3,4-trifluoronitrobenzene are added dropwise at 70° C. (30 min). The mixture is kept at this temperature for 20 h; after this time, GC analysis shows 57% of 2,3-difluoro-6-nitrobenzonitrile and 43% of 2,3,4-trifluoronitrobenzene, based on volatile components, in the dark black reaction mixture. After cooling, the solid residue is filtered off with suction and the solvent is distilled off. According to GC analysis, the distillate contains 15.2 g (86 mmol) of 2,3,4-trifluoronitrobenzene, which were not reisolated. The black residue (31.7 g) is dissolved in 300 ml of dichloromethane and filtered through silica gel. The entire filtrate (yellow) is evaporated on a rotary evaporator to remove the solvent, and adhering 2,3,4-trifluoronitrobenzene residues are removed from the beige-colored residue under vacuum to give 24.8 g (0.135 mol, 54% of theory, 82% of theory based on converted 2,3,4-trifluoronitrobenzene) of 2,3-difluoro-6-nitrobenzonitrile, which has a sufficient purity (GC>95%) for further reaction, but of which a small amount is purified by preparative thin layer chromatography for analytical purposes.

If the reaction is carried out in 200 g of N,N-dimethylacetamide (DMAc) rather than in tert-butanol, using 14 7 g (0 3 mol) of sodium cyanide at 40° C. starting material can no longer be detected after 8 h. After the insoluble residue has been filtered off, about 150 g of the solvent are distilled off and 150 g of water are added, with stirring. The crude product which has precipitated out is filtered off with suction at 0° C. and dried (30.7 g, purity (GC) ca. 85%). The substance can be used in the next step without further purification.

2,3-Difluoro-6-nitrobenzonitrile: M.p. (DSC): 51.5° C. $C_7H_2F_2N_2O_2$ (184.102) (% by weight) calc. C 45.67 H 1.09 F 20.64 N 15.22 found C 45.2 H 1.3 F 20.6 N 15.2

IR (KBr, cm$^2$): 3420, 3090, 2250, 1600, 1545, 1495, 1455, 1350, 1290, 1245, 1140, 1020, 855, 820, 765, 720, 700, 640, 600

$^1$H NMR [CDCl$_3$/ppm]: δ=7.69 (dd, 1H, Ar-H$^4$) 8.24 (ddd, 1H, Ar-H$^5$)

$^{19}$F NMR [CDCl$_3$/ppm]: δ=−122.73 (ddd, 1F, Ar-F$^3$) −123.78 (ddd, 1F, Ar-F$^2$)

MS: m/z (%)-46 (8), 61 (14), 68 (11), 75 (24), 87 (20), 88 (99), 99 (10), 112 (26), 126 (38), 138 (42), 154 (11), 167 (5), 184 (100)

Example 2

24.8 g (0.135 mol) of 2,3-difluoro-6-nitrobenzonitrile and 1 g of anhydrous calcium chloride are placed in a 50 ml flask with a finely drawn-out gas inlet tube, and heated to 190° C. Chlorine is introduced at this temperature with a throughput of 2–3 l/h so that a uniform production of nitrous gases occurs. After a reaction time of 12 h, the starting material has been substantially converted (<10% residual content of nitro compound). The remaining nitrous gases are purged with air and the residue is distilled off under vacuum over a short Vigreux column to give 15.5 g (89 mmol, 66%) of 2-chloro-5,6-difluorobenzonitrile as a light yellowish, oily liquid boiling at 70°–75° C./3 Torr (purity (GC)>95%).

2-Chloro-5,6-difluorobenzonitrile:

$^1$H NMR [CDCl$_3$/ppm]: δ=7.30 (ddd, 1H, $J_{BC}$=1.80 Hz, $J_{BD}$=3.99 Hz, $J_{AB}$= 9.01 Hz, Ar-H$^3$ (B)) 7.41 (ddd, 1H, $J_{AC}$=7.95 Hz, $J_{AD}$=9.05 Hz, $J_{AB}$= 9.01 Hz, Ar-H$^4$ (A))

$^{19}$F NMR [CDCl$_3$/ppm]: δ=−126.22 (ddd, 1F, $J_{BC}$=1.80 Hz, $J_{AC}$=7.95 Hz, $J_{CD}$=20.14 Hz, Ar-F$^5$ (C)) −136.18 (ddd, 1F, $J_{BD}$=3.99 Hz, $J_{AD}$=9.05 Hz, $J_{CD}$=20.14 Hz, Ar-F$^6$ (D))

MS: m/z (%)=61 (6), 68 (5), 75 (6), 87 (9), 88 (22), 93 (4), 99 (4), 112 (6), 118 (4), 137 (6), 138 (19), 146 (3), 148 (1), 173 (100, M+), 174 (9), 175 (34), 176 (3)

Example 3

A suspension of 5.8 g (0.1 mol) of potassium fluoride in 60 g of sulfolane is dried by distilling off 10 g of the solvent. 0.2 g of tetra-n-butylphosphonium bromide and 15.5 g (89mmol) of 2-chloro-5,6-difluorobenzonitrile are added and the mixture is heated at 190° C. for 8 h. After this time, the starting material has been completely converted. After cooling, the salt is filtered off and rinsed with 20 g of warm sulfolane, and 2,3,6-trifluorobenzonitrile is distilled off from the liltrate over a short Vigreux column to give 9.8 g (62 mmol, 70%) of a substance with a purity of >90% (sulfolane being the main impurity), which are used in the hydrolysis without further purification.

Example 4 (Hydrolysis Example)

9.8 g (63 mmol) of 2,3,6-trifluorobenzonitrile are added dropwise over 15 min, at 150° C., to 20 g of 75 percent sulfuric acid. After 3 h, nitrile can no longer be detected The solution, at 100° C. is poured on to 50 g of ice and the mother liquor is extracted with methyl tert-butyl ether (MTBE). Drying over magnesium sulfate and removal of the solvent gives 10.1 g (91%, 57 mmol) of 2,3,6-trifluorobenzoic acid as light yellowish crystals, which can be further purified by recrystallization from water (15 g) (melting point 123°–125° C.).

What is claimed is:

1. A process for the preparation of 2,3-difluoro-6 -nitrobenzonitrile from 2,3,4-trifluoronitrobenzene, comprising:

reacting each mole of 2,3,4 -trifluoronitrobenzene with 1 to 5 moles of an alkali metal, alkaline earth metal or transition metal cyanide in the presence of a solvent reaction medium at a temperature of from about 20° to about 120° C., and recovering the 2,3-difluoro-6 -nitrobenzonitrile from the solvent reaction medium in a yield of at least about 54% of theory and a purity of at least about 85%.

2. The process as claimed in claim 1, wherein the amount of cyanide is 1.1 to 3 mol per mole of 2,3,4-trifluoronitrobenzene.

3. The process as claimed in claim 1, wherein the cyanide is sodium, potassium, or copper cyanide.

4. The process as claimed in claim 1, wherein the solvent reaction medium comprises a protic or aprotic polar solvent.

5. The process as claimed in claim 1, wherein the amount of said solvent reaction medium is 100% to 2000% by weight, based on the weight of the 2,3,4-trifluoronitrobenzene.

6. The process as claimed in claim 1, wherein the solvent reaction medium comprises at least one of the following polar aprotic solvents: acetone, tetrahydrofuran, acetonitrile, 1,2-dimethoxyethane, tetramethylenesulfone, tetramethylene sulfoxide, N,N-diethylacetamide, N,N-dimethylacetamide, N,N-dimethylformamide, N-methylpyrrolidone, dimethyl sulfoxide, dimethyl sulfone, diphenyl sulfoxide, diphenyl sulfone, tetramethylurea, tetra-n-butylurea, or 1,3-dimethylimidazolidin-2-one.

7. The process as claimed in claim 1, wherein the solvent reaction medium comprises a protic solvent.

8. The process as claimed in claim 7, wherein said protic solvent is water or a tertiary alcohol.

9. The process as claimed in claim 8, wherein the tertiary alcohol is tert-butanol, and the purity of the 2,3-difluoro-6-nitrobenzonitrile is greater than 95%.

10. The process as claimed in claim 1, wherein said reacting step is carried out at a temperature in the range of from 40° to 80°.

11. The process as claimed in claim 1, wherein the resulting 2,3-difluoro-6-nitrobenzonitrile, essentially without purification, is chlorinated with a chlorinating agent elevated temperature, optionally in the presence of a fluoride-trapping or dehydrating agent, to give 2-chloro-5,6-difluorobenzonitrile.

12. The process as claimed in claim 11, wherein the chlorinating agent is chlorine, phosphorous trichloride or phosphorus pentachloride.

13. The process as claimed in claim 12, wherein the chlorinating agent is chlorine.

14. The process as claimed in claim 11, wherein said elevated temperature ranges from 130° to 250° C.

15. The process as claimed in claim 14, wherein said elevated temperature ranges from 160° to 200°.

16. The process as claimed in claim 14, wherein said elevated temperature ranges from 170° to 190°.

17. The process as claimed in claim 11, wherein the 2,3-difluoro-6-nitrobenzonitrile is chlorinated in the presence of at least one of the following fluoride-trapping or dehydrating agents: calcium chloride, calcium hydroxide, calcium sulfate, silicon dioxide, phosphorus pentachloride or phosphorus pentoxide.

18. The process as claimed in claim 11, wherein the chlorinating agent is chlorine, and said 2,3-difluoro-6-nitrobenzene is chlorinated with about 10 to about 400 ml/g.h of chlorine.

19. The process as claimed in claim 18, wherein said 2,3-difluoro-6-nitrobenzene is chlorinated with 20 to 200 ml/g.h of chlorine.

20. The process as claimed in claim 11, wherein the amount of chlorinating agent is 0.5 to 20 mol per mol of 2,3-difluoro-6-nitrobenzonitrile.

21. The process as claimed in claim 20, wherein the amount of said chlorinating agent is 0.7 to 3 mol of 2,3-difluoro-6-nitrobenzonitrile.

22. The process as claimed in claim 11, wherein said 2,3-difluoro-6-nitrobenzonitrile is chlorinated at greater than atmospheric pressure.

23. The process as claimed in claim 11, wherein the resulting 2-chloro-5,6-difluorobenzonitrile is fluorinated with an alkali metal fluoride to give 2,3,6-trifluorobenzonitrile.

24. The process as claimed in claim 23, wherein the resulting 2,3,6-trifluorobenzonitrile, essentially without purification, is hydrolyzed to 2,3,6-trifluorobenzoic acid.

25. The process as claimed in claim 23, wherein the 2-chloro-5,6-difluorobenzonitrile is fluorinated in a closed fluorination zone at greater than atmospheric pressure.

* * * * *

UNITED STATES PATENT AND TRADEMARK OFFICE
CERTIFICATE OF CORRECTION

PATENT NO. : 5,478,963
DATED : December 26, 1995
INVENTOR(S) : Ralf Pfirmann, et. al.

It is certified that error appears in the above-indentified patent and that said Letters Patent is hereby corrected as shown below:

In claim 11 (at column 7, lines 31 and 32), please insert the word --at-- after the word "agent" and before the word "elevated".

Signed and Sealed this

Fourth Day of June, 1996

Attest:

BRUCE LEHMAN

Attesting Officer

Commissioner of Patents and Trademarks